United States Patent [19]

Rapoport

[11] Patent Number: 4,714,773

[45] Date of Patent: Dec. 22, 1987

[54] HYDROCYANATION OF BUTADIENE

[75] Inventor: Morris Rapoport, Orange, Tex.

[73] Assignee: E. I. Du Pont de Nemours and Company, Wilmington, Del.

[21] Appl. No.: 5,431

[22] Filed: Jan. 9, 1987

[51] Int. Cl.⁴ .......................................... C07C 120/02
[52] U.S. Cl. ................................................ 558/338
[58] Field of Search ........................................ 558/338

[56] References Cited

U.S. PATENT DOCUMENTS 3,496,215 2/1970 Drinkard et al. .................... 558/338
3,903,120 9/1975 Shook, Jr. et al. ............. 558/338 X
4,330,483 5/1982 Rapoport ............................ 558/338

Primary Examiner—Joseph P. Brust

[57] ABSTRACT

Hydrocyanation of butadiene using a mixed ligand zerovalent nickel catalyst wherein the mixture of phosphite ligands there is 10 to 65 mol percent phenyl, and a complemental amount of meta- and para-tolyl.

8 Claims, No Drawings

HYDROCYANATION OF BUTADIENE

FIELD OF THE INVENTION

This invention relates to the production of 3-pentenenitrile and 4-pentenenitrile (3,4-pentenenitriles) by the hydrocyanation of butadiene (BD) using a zerovalent nickel catalyst.

BACKGROUND

The hydrocyanation of butadiene using a nickel catalyst of the formula $Ni[P(OR)_3]_4$ is disclosed in Drinkard et al. U.S. Pat. No. 3,496,215. R in the Drinkard et al. formula may be an aryl of up to 18 carbon atoms. Examples XI and XII of said patent show reacting butadiene and hydrogen cyanide in the presence of a nickel catalyst of the above formula where R is phenyl.

A process for the preparation of zerovalent nickel complexes from elemental nickel are disclosed in Shook et al. U.S. Pat. No. 3,903,120. Among the various complexes disclosed by Shook et al. Are the mixed ligand complexes where the ligand is a mixed tri-meta- and para-tolyl phosphite—see Example 12 and Table 1, and complexes where the ligands are a mixture of ortho-tolyl and phenyl—see Example 54.

Hydrocyanation of pentenenitriles using a mixed ligand zerovalent nickel catalyst, in which the ligands are phosphite esters of mixtures of phenol, meta-cresol and para-cresol, are disclosed in Rapoport U.S. Pat. No. 4,330,483—see footnote 6 to the table appearing in Columns 5 and 6.

Some commercial processes for the hydrocyanation of butadiene have used zerovalent nickel catalysts of the formula $Ni[P(OR)_3]_4$ in which the ligands are phosphite esters of mixtures of meta- and para-cresol.

SUMMARY OF THE INVENTION

It has now been found that if the hydrocyanation of butadiene to form a product mixture containing 3-pentenenitrile and 4-pentenenitrile is carried out using a zerovalent nickel catalyst of the formula $Ni[P(OR)_3]_4$ where the ligand is comprised of phosphite esters of mixtures of phenol, meta-cresol and para-cresol, i.e., R is a mixture of phenyl, meta- and para-tolyl, that yield losses to by-products are substantially diminished. The phenyl content of the total ligand [free and combined with Ni(O)] should be in the range of about 10 to 65 percent and the meta-, para-tolyl content should be about 35 to 90 percent, i.e., the meta-, para-tolyl components should be present in a complemental amount. The ratio of meta-tolyl to para-tolyl may vary from 0.5/1 to 3.5/1 but the range of 1/1 to 2.5/1 is preferred. The preferred range for phenyl is 25 to 50 mol percent. These percentages are based on the total aromatic alcohol employed in the preparation of the ligand.

In carrying out the hydrocyanation of butadiene, the feed molar ratio of ligand $[P(OR)_3]$ to zerovalent nickel [Ni(O)] should be in the range of 8/1 to 30/1, and preferably in the range of 10/1 to 20/1. The hydrocyanation reaction can be carried out at a temperature in the range of 25° to 200° C., but is preferably carried out at a temperature in the range of 50° to 150° C. The reaction may be carried out in a single stage or in multiple stages. If multistaged, the stages are arranged in series with the effluent from an initial stage being directed to the next or subsequent stage. If the reaction is carried out stagewise the hydrogen cyanide is introduced into two or more stages. The overall feed mol ratio of hydrogen cyanide to butadiene may vary from 0.5/1 to 1/1. The preferred overall feed mol ratio, HCN/BD, is from 0.75/1 to 0.95/1.

Commercial grade phenol and the commercial grade mixture of meta- and para-cresol are satisfactory sources of reactants with phosphorus trichloride to form the ligands of the zerovalent nickel catalyst. The reaction conditions set forth in Shook et al. U.S. Pat. No. 3,903,120 are satisfactory for the preparation of the catalyst.

EXAMPLES

Continuous single stage butadiene hydrocyanations were run as described below:

An approximately 39 cc agitated reaction vessel was fed three separate liquid ingredients, butadiene (BD, dried by mol sieve), hydrogen cyanide (HCN, unstabilized) and catalyst by three syringe pumps, each of 375 cc capacity. The reaction vessel which was fitted with a thermocouple and a pressure relief device was heated by an electric hot air blower. The current in the blower heater coil was controlled by an electronic controller.

The back pressure on the vessel was maintained by a pneumatically controlled valve. The reactions were run at 110° C. and about 200 psig. The reactor was run liquid filled.

The product exiting the reactor flowed into a flasher vessel (310 cc) where unreacted BD could be vented through a wet test meter and from which the liquid reaction contents were periodically drained.

At start-up the reactor was filled with catalyst, then only catalyst and BD were continuously fed to the reactor until the BD off-gas readings from the wet test meter stabilized. Then HCN was continuously introduced. As the BD reacted with the HCN the BD off-gas flow as measured by the wet test meter gradually decreased and stabilized. When sufficient time had elapsed (usually by three or four reactor turnovers) the flasher was completely drained. Then product liquid was again allowed to accumulate in the flasher and periodically completely drained and weighed to provide samples for analysis. This procedure was repeated about five times to obtain sample weights averaging about 50 g. The analytical results of the steady state samples were then averaged before yield calculations.

The results are summarized in the Table. The results show that for comparable BD conversions the yield loss to by-products was always less with a phenol mixed ligand catalyst.

TABLE

| Example No. | Mol % Phenol in Catalyst Prep. | % BD Conv. | Total % Yield Loss | Feed Lig/ Ni(O) Ratio | Overall Feed % Ligand | Rate × 1000 Grams/ cc-min |
|---|---|---|---|---|---|---|
| 1 | 25 | 84.0 | 2.7 | 11.8 | 49.9 | 9.9 |
| 2 | 25 | 88.7 | 2.6 | 11.8 | 50.0 | 9.6 |
| 3 | 50 | 88.8 | 2.3 | 13.1 | 52.5 | 9.8 |
| Control 1 | <0.1 | 81.4 | 3.8 | 12.7 | 50.0 | 9.4 |
| Control 2 | <0.1 | 83.7 | 4.1 | 12.7 | 50.0 | 8.6 |
| Control 3 | <0.1 | 87.1 | 5.5 | 12.7 | 49.9 | 8.3 |
| Control 4 | <0.1 | 88.6 | 5.9 | 12.7 | 49.7 | 8.8 |
| Con- | <0.1 | 89.7 | 7.3 | 12.7 | 49.8 | 8.8 |

TABLE-continued

| Example No. | Mol % Phenol in Catalyst Prep. | % BD Conv. | Total % Yield Loss | Feed Lig/Ni(O) Ratio | Overall Feed % Ligand | Rate × 1000 Grams/cc-min |
| --- | --- | --- | --- | --- | --- | --- |
| trol 5 | | | | | | |

The mol % phenol in catalyst refers to the sum of the three ingredients, phenol, m-cresol and p-cresol.
The ratio of m-cresol to p-cresol was 2.2/1.
In the column titled "Feed Lig/Ni(O) Ratio" Lig is total ligand free and combined with Ni(O).
The total % yield loss refers to the sum of the yield losses to 2-pentenenitriles, 2-butenenitriles, intermediate boilers and methylglutaronitrile. Methylglutaronitrile and 2-butenenitriles are the major yield losses. Most of the yield improvement is in reduced methylglutaronitrile.
The rate refers to the rate of useful products, 3-pentenenitrile, 4-pentenenitrile and 2-methyl-3-butenenitrile. [2-methyl-3-butenenitrile can be isomerized to a mixture of 3-pentenenitrile and 4-pentenenitrile.]

I claim:

1. A continuous process for the production of 3,4-pentenenitriles which comprises reacting butadiene and hydrogen cyanide in the presence of a zerovalent nickel catalyst of formula Ni[P(OR)$_3$]$_4$ and excess ligand having the formula P(OR)$_3$ where 10 to 65 mol percent of the R groups are phenyl and 35 to 90 mol percent of the R groups are mixed meta- and para-tolyl, where the ratio of meta- and para-tolyl is in the range of 0.5/1 to 3.5/1, and where the feed molar P(OR)$_3$/Ni(O) ratio is in the range from 8/1 to 30/1, and the feed molar ratio of hydrogen cyanide to butadiene is in the range of 0.5/1 to 1/1, and the reaction temperature is in the range of 25° to 200° C.

2. The process of claim 1 where 25 to 50 mol percent of the R groups are phenyl and a complemental amount are mixed meta- and para-tolyl.

3. The process of claim 1 where the ratio of meta-tolyl to para-tolyl is in the range from 1/1 to 2.5/1.

4. The process of claim 1 where the feed hydrogen cyanide/butadiene mol ratio is in the range from 0.75/1 to 0.95/1.

5. The process of claim 1 where the hydrocyanation reaction is carried out in multiple stages.

6. The process of claim 1 where the feed molar ratio P(OR)$_3$/Ni(O) in the catalyst stream is in the range from 10/1 to 20/1.

7. The process of claim 1 where the reaction temperature is in the range from 50° to 150° C.

8. A continuous process for the production of 3,4-pentenenitriles which comprises reacting butadiene and hydrogen cyanide in the presence of a catalyst consisting of a zero-valent nickel catalyst of the formula Ni[P(OR)$_3$]$_4$ and excess ligand having the formula P(OR)$_3$ where 10 to 65 mol percent of the R groups are phenyl and 35 to 90 mol percent of the R groups are mixed meta- and para-tolyl, wherein the ratio of meta- to para-tolyl is in the range 0.5/1 to 3.5/1, and where the feed molar P(OR)$_3$/Ni(O) ratio is in the range from 8/1 to 30/1, and the feed molar ratio of hydrogen cyanide to butadiene is in the range of 0.5/1 to 1/1, and the reaction temperature is in the range of 20°–200° C.

* * * * *